US008938301B2

(12) United States Patent
Hagedorn (10) Patent No.: US 8,938,301 B2
(45) Date of Patent: Jan. 20, 2015

(54) HEADGEAR WITH DISPLACEABLE SENSORS FOR ELECTROPHYSIOLOGY MEASUREMENT AND TRAINING

(71) Applicant: Evoke Neuroscience, Inc., Jacksonville, NC (US)

(72) Inventor: David W Hagedorn, Jacksonville, NC (US)

(73) Assignee: Evoke Neuroscience, Inc., Jacksonville, NC (US)

( * ) Notice: Subject to any disclaimer, the term of this patent is extended or adjusted under 35 U.S.C. 154(b) by 0 days.

(21) Appl. No.: 14/458,673

(22) Filed: Aug. 13, 2014

(65) Prior Publication Data

US 2014/0350431 A1    Nov. 27, 2014

Related U.S. Application Data

(63) Continuation-in-part of application No. 13/742,066, filed on Jan. 15, 2013, now Pat. No. 8,838,247, which is a continuation of application No. 13/543,204, filed on Jul. 6, 2012, now Pat. No. 8,380,316, which is a continuation of application No. 12/979,419, filed on Dec. 28, 2010, now Pat. No. 8,239,030.

(60) Provisional application No. 61/292,791, filed on Jan. 6, 2010.

(51) Int. Cl.
| | |
|---|---|
| *A61N 1/00* | (2006.01) |
| *A61B 5/0478* | (2006.01) |
| *A61N 2/00* | (2006.01) |
| *A61B 5/00* | (2006.01) |
| *A61B 5/0482* | (2006.01) |
| *A61N 1/36* | (2006.01) |
| *A61N 1/04* | (2006.01) |

(52) U.S. Cl.
CPC .............. *A61B 5/0478* (2013.01); *A61N 2/004* (2013.01); *A61B 5/6814* (2013.01); *A61N 2/006* (2013.01); *A61B 5/0482* (2013.01); *A61B 5/6803* (2013.01); *A61N 1/36025* (2013.01); *A61N 1/0484* (2013.01)
USPC .......................................................... 607/45

(58) Field of Classification Search
USPC .......................................................... 607/45
See application file for complete search history.

(56) References Cited

U.S. PATENT DOCUMENTS

| | | | |
|---|---|---|---|
| 2002/0029005 A1* | 3/2002 | Levendowski et al. ........ | 600/545 |
| 2009/0088619 A1* | 4/2009 | Turner et al. .................. | 600/383 |

* cited by examiner

*Primary Examiner* — Robert N Wieland
(74) *Attorney, Agent, or Firm* — Bechen PLLC (57) ABSTRACT

A method and system provides for headgear usable for electrophysiological data collection and analysis and neurostimulation/neuromodulation or brain computer interface for clinical, peak performance, or neurogaming and neuromodulation applications. The headgear utilizes dry sensor technology as well as connection points for adjustable placement of the bi-directional sensors for the recoding of electrophysiology from the user and delivery of current to the sensors intended to improve or alter electrophysiology parameters. The headgear allows for recording electrophysiological data and biofeedback directly to the patient via the sensors, as well as provide low intensity current or electromagnetic field to the user. The headgear can further include auditory, visual components for immersive neurogaming. The headgear may further communication with local or network processing devices based on neurofeedback and biofeedback and immersive environment experience with balance and movement sensor data input.

20 Claims, 5 Drawing Sheets

HEADGEAR WITH DISPLACEABLE SENSORS FOR ELECTROPHYSIOLOGY MEASUREMENT AND TRAINING

PRIORITY CLAIMS

The present Application is a Continuation-in-part of and claims priority to U.S. patent application Ser. No. 13/742,066 filed Jan. 15, 2013, which is a continuation of and claims priority to U.S. patent application Ser. No. 13/543,204, filed Jul. 6, 2012, issued as U.S. Pat. No. 8,380,316, which is a continuation of and claims priority to U.S. patent application Ser. No. 12/979,419, filed Dec. 28, 2010, issued as U.S. Pat. No. 8,239,030, which is based on and claims priority to U.S. Provisional Patent Application Ser. No. 61/292,791 filed Jan. 6, 2010.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF INVENTION

The disclosed technology relates generally to the headgear providing measurement, neuromodulation and feedback sensors for neurological measurements and modulation by delivery of current to sensors. More specifically, the technology relates to headgear having attachable and moveable wet or dry sensor technology, as well as feedback processing functionality for electrophysiology measuring, testing and feedback.

BACKGROUND

Traumatic brain injuries can result in physical and/or emotional dysfunction. Post traumatic stress disorder (PTSD) symptoms are similar to those of a mild traumatic brain injury (mTBI) and the two are difficult to differentiate using current assessment methodologies such as symptom assessments and questionnaires.

The brain is composed of about 100 billion neurons, more than 100 billion support cells and between 100 and 500 trillion neural connections. Each neuron, support cell and neural connection is extremely delicate, and the neural connections are tiny (approximately 1 micrometer). When the brain moves within the skull, such as occurs in rapid acceleration/deceleration (e.g., exposure to sudden impact and/or explosive devices), axons within the brain can pull, stretch and tear. If there is sufficient injury to the axon or support cells, the cell will die, either immediately or within a few days. Such damage can occur not only in the region that suffered direct trauma but in multiple regions (e.g., diffuse axonal injury).

Wearable wireless transmitting physiology sensors and digital recording and processing of these human physiology measurements have permitted new technologies to measure and modify human physiology and to treat disorders from remote locations around the world.

Prior headgear techniques utilize dry sensor technology, which is expensive, uncomfortable for scalp contact applications, and with unreliable signal quality over areas covered by hair. As a result only saline and gel based connection solutions have permitted adequate signal quality with more comfortable electrode contact to skin. These limitations have resulted in little use of electrophysiology measures and brain computer interface interventions that are for the most part side effect free.

Further, the design of caps and headsets have been such that users will only wear them for hospital or clinical applications and not for daily use where fashion pressures guide wearable technology decisions and behavior. The lack of fashionable aspects to the headgear, as well as the headgear lacking properly integrated audio and/or visual outputs, limits usage of the underlying technology.

Finally, the software interface has lacked a level of gaming engagement that further reduces ones interest to use the technology, no matter the clinical and peak performance benefits. With the advent of no contact sensor technology and new electronics able to fit into very small and flexible circuit boards with wireless low energy demands, electrophysiology measurement and training technology can be crafted into aesthetically appealing forms that coincide with current fashion trends.

The ability for a high fashion worthy design to coexist with dry sensor technology is further advanced when joined with neurogaming software that is interactive and modified by the users own electrophysiology. Game play is both enjoyable and physiologically enhancing such that users can play games while unknowingly developing improved cognitive and emotional processing.

The ability for a mobile design to coexist with dry sensor technology and visual tracking technology and be worn in natural environments that is further advanced when joined with neuromarketing software that quantify user interest in displayed products and related marketing needs presented to the user. Worn neuromarketing headset is both comfortable and captures electrophysiology paired in real time to visual tracking of stimuli such that users and marketing assessment entities can obtain enhanced information about user preference.

As such, there exists a need for improved headgear integrating sensor technology for use with neuro data collection and processing software for improved user access and functionality.

BRIEF DESCRIPTION

A high-end head wearable speaker system allows a user to listen to music, take phone calls, and also engage games with the power and personal control of brain and heart and balance. Using ultra high impedance electrophysiological sensors, it is now possible to record EMG signals, ECG signals and/or EEG signals at the surface of the skin more easily and reliably than with prior technologies. When combined with ultra-high impedance movement sensors there is now the ability to reduce disruptive artifact thereby permitting cleaner physiological signal for analysis. The non-contact solid state electric potential sensor can be used to identify movement at or near the sensor connection point and thereby control for a cleaner or artifact free signal output.

At the sensor or electrode point, a magnetic connector is part of the sensor/electrode so that the sensor can be easily attached to the headset along a conductive track and similarly removed for cleaning or rapid replacement with the same or alternate style sensors.

The system and method and underlying technology provides for the collection of physiology data for remote processing and returned feedback via the headgear. Therein, the headgear facilitates various types of operations, including clinical use applications, personal data collection or biohacking operations, gaming operations, amongst others.

For example, with gaming operations, one embodiment includes a hand-held tablet that displays the game while a wireless electrophysiology signal is processed on the headset streaming EEG, heart rate, and movement/balance data to the game interface for a real time human brain and heart function interplay. Automated scripted software permit untrained users to collect electrophysiology data for measurement and diagnostic purposes while also offering real time brain computer interface training or therapy.

The system and method includes headgear technology with improved sensor technology, as well as improved usage characteristics where the collection of data using one or more data collection techniques. These techniques may include the performance of one or more tests using electrophysiology equipment, including wired and/or wireless equipment. The testing data is then collected, collated, assembled and may be pre-processed as necessary. The data is then transmitted to one or more central processing devices for the performance of processing operations thereon.

In the real-time network-based or cloud-based processing technique, the data is processed and managed. Variety of processing operations are performed on the data to better understand and analyze the data, as well as catalog and centrally store the data.

In accordance with these and other objects, which will become apparent hereinafter, the disclosed technology will now be described with particular reference to the drawings.

A better understanding of the disclosed technology will be obtained from the following detailed description of the preferred embodiments taken in conjunction with the drawings and the attached claims.

DETAILED DESCRIPTION

Various embodiments are described herein, both directly and inherently. However, it is understood that the described embodiments and examples are not expressly limiting in nature, instead illustrate examples of the advantageous uses of the innovative teachings herein. In general, statements made in the specification of the present application do not necessarily limit any of the various claimed inventions and it is recognized that additional embodiments and variations recognized by one or more skilled in the art are incorporated herein.

As noted above, the improved headgear includes improvements in sensor connections, fashionable aspects, usability and integration of audio and/or video stimuli, for the measurement of electrophysiology data. The data is collected and processed in a local or networked or server-based processing environment.

Figure 1:
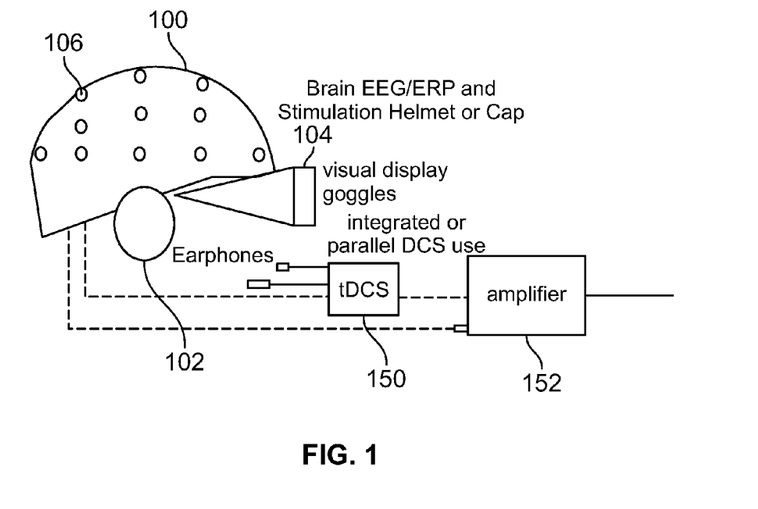
FIG. 1 illustrates one embodiment of a device for taking measurements.

FIG. 1 illustrates a measurement device used to measure the initial data. A helmet 100 comprises at least one, or a plurality of, electrodes 106 (represented as white dots). The helmet may be any receptacle that holds the electrodes in a position relative to the head of a wearer, or alternatively, electrodes may be taped or otherwise placed on the head. The helmet 100 may also be updated using the headgear described below, wherein the headgear incorporates various helmet 100 aspects. Earphones 102, goggles 104 and/or another display device (e.g. a small high-resolution display) are used to exhibit stimuli to a user, integrate with visual tracking software, the stimuli used to vary measurable brain and heart function and balance activity.

The electrodes 106 are electrically connected to one of an electrical stimulation device 150 or electrical measuring device (e.g., a sensor), such as by way of amplifier 152. The same electrode or electrodes may be disconnected from one such device and connected to another such device, such as by way of changing an electrical pathway (switch) or by physically disconnecting an electrical wire from one device, and plugging into another. Other devices, not shown, include force platforms (measure postural deviations of person), devices to alter the display on the goggles 104, and devices to alter the sound through the earphones 102, and input devices such as a computer mouse, keyboards, and joysticks.

Referring now to visual stimuli exhibited on a display device, such as the goggles 104 of FIG. 1, the visual stimuli produced may be an "immersive environment," for example a virtual reality 2- or 3-dimension moving "room" displayed through a virtual reality headset. The data collected from the balance plate, heart rate monitor, EEG, and so forth, can be used in conjunction with the visual stimuli for neurophysiological trauma assessment and/or rehabilitation training. The data collected from this component, as well as all other components may be linked with data collected from other components (e.g., EEG, ERP, ECG, balance) for assessment purposes.

The system shown in FIG. 1 may further comprise a vestibular activation test (VAT) headset permitting a computerized test that monitors the vestibulo-ocular reflex (VOR) during natural motion. A VAT headset useful for the systems described herein may produce images and/or record eye movements. Images displayed in the VAT headset may be generated by computer-implemented instructions and transmitted via electrical impulses to the VAT headset via wireless or direct connection. Eye movements may be recorded by way of the VAT headset. The VOR is a reflex eye movement that stabilizes images on the retina during head movement by producing an eye movement in the direction opposite to head movement, thus preserving the image on the center of the visual field. As ocular trauma is often concomitant with traumatic brain injury, this component allows additional assessment of injury.

The measurements of electrophysiological data of a patient may include measurements acquired from dry or wet sensors or functional near infrared spectroscopy (fNIRs) optical fibers that send light into the scalp at wavelengths in the range of 650-850 nms. The sensors and/or fNIRs may be attached to the non-invasive brain stimulation or modulation helmet/cap described herein.

Moreover, for clarity purposes, as used herein, a patient may refer to an individual under direct care or supervision of a doctor, but a patient is not so limited and may further include any suitable user or client wherein measurement data is acquired and analyzed as described herein. For example, a patient may include non-medically related uses, such as an athlete and the review/analysis of electrophysiological data of an athlete to analyze possible concussion data. Another example of a patient may be soldiers with the review/analysis of electrophysiological data of the soldiers to analyze data relative to possible traumatic brain injury or post traumatic stress disorder.

Figure 2:
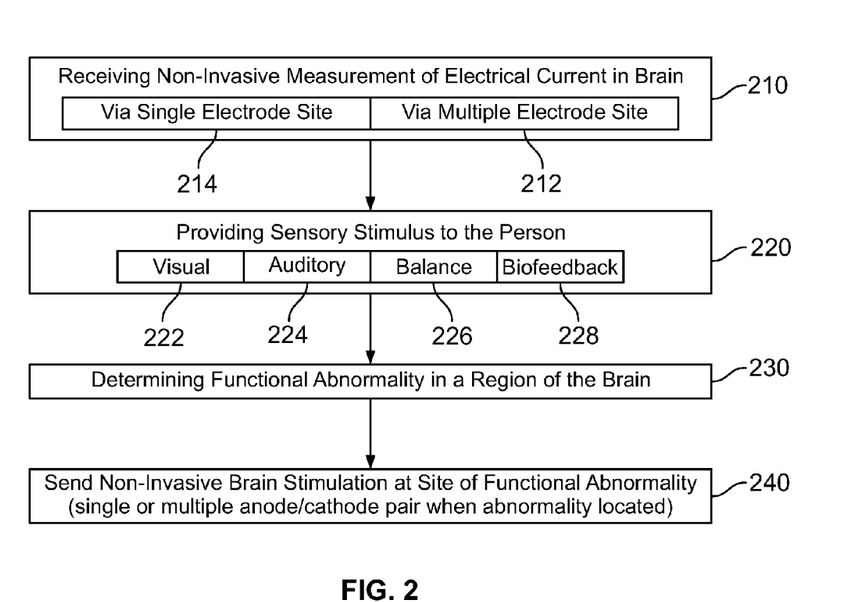
FIG. 2 illustrates one embodiment of a block diagram of a method for carrying measurements.

FIG. 2 shows a high level block diagram of a method for acquiring the measurements. In step 210, non-invasive measurements are made of electrical current in the brain of a test subject. This is accomplished by way of electrodes placed on a test subject, such as in a helmet shown in FIG. 1. In this manner, EEG and ERP signals may be recorded, measured, and analyzed. A single electrode may be used to carry out the measuring in step 214, or a plurality of electrode pairs may be used in step 212. The position of the electrodes is known, and each electrode or a grouping thereof is placed over a definable region of the brain, the region defined by a person carrying out embodiments of the disclosed technology. The region is defined as a specific brain area of interest for the recording, as defined by a person carrying out embodiments of the disclosed technology and may be a region covered by a single electrode pair or as large as half a hemisphere of a brain. Electrodes may also be grouped into clusters, such as with a single anode surrounded by three or more cathodes, or a single cathode surrounded by three or more anodes. Such clusters are electrically connected, such that electric current flows non-invasively through the proximal tissue from anode(s) to cathode(s), stimulating the brain (stimulating, herein is defined as passage of electrical current through the brain and includes increasing or decreasing neuron activity at a site). Thereby, the system can provide neurostimluation and/or neuromodultion to the user.

While conducting step 210, typically, step 220 is also carried out which comprises providing sensory stimulus to a person. This may be done by way of, for example, the goggles shown in FIG. 1 for a visual stimulation 222, auditory stimulation 224, balance stimulation 226, biofeedback measurements 228, or other sensory stimulations known in the art.

Stress tests and peak performance tests may also be performed to determine, for example, how many times a minute a person is able to respond to a stimulus, or how long a person can hold his/her breath or balance on a force platform, etc.

Based on the electrical measurements, that is, EEG or ERP measurements, an abnormality in a region of the brain is determined in step 230. An abnormality may be any of the following: electrical activity which is too infrequent, too frequent, too low in amplitude, too large in amplitude, an improper pattern of electrical activity, inter-intra-hemispheric connectivity, electrical activity in the wrong portion of the brain for the stimulus given, or the like.

In step 240, based on the located functional abnormality, non-invasive brain stimulation (such as tDCS or tACS) is administered at the region of the Abnormality. In certain cases, the same electrode which was used to measure the electrical impulses within the brain is used to administer tDCS, tACS, or other electrical stimulation. In this manner, accuracy of the stimulated region may be assured, as there is no difference in the physical location on the head where the existing electrical impulse was measured, versus where the new electrical stimulation is administered. The place of administering may be as little as a single anode/cathode pair (or cluster), or may use multiple anode/cathode pairs (or clusters).

Figure 3:
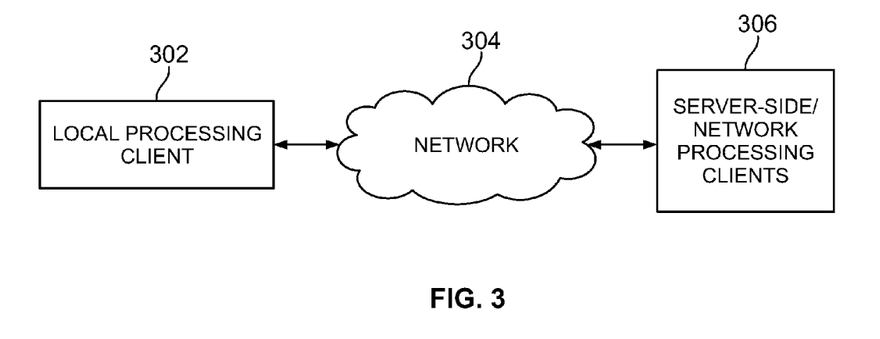
FIG. 3 illustrates one embodiment of a processing environment for the measurements and processing described herein.

Whereby the device of FIG. 1 provides for collection of data, FIG. 3 illustrates an embodiment of processing environment providing for the remote database and data analysis method and system operations. In this system, the local processing client 302 may be any suitable local processing device including but not limited to the collection of measurement data, and/or one or more processing systems for executing interface operations. For example, in one embodiment the local processing client may be a personal computer or a tablet computer having a browser or application for executing the interface functionality described herein.

The network 304 may be any suitable network providing communication thereacross. In one embodiment, the network 302 is an Internet connection across a public access network, wherein it is recognized that the network may include a private and/or secure network, as well as network exchanges via one or more service providers. The network 304 operates to facilitate the communication of data between the local processing client 302 and the server-side network processing clients 306.

The server-side network processing clients 306 may be any suitable number of network-processing devices. In one embodiment, the client 306 may be a dedicated processing server, wherein in another embodiment, the client 306 may be any suitable number of distributed computer resources for processing operations as described herein.

Figure 4:
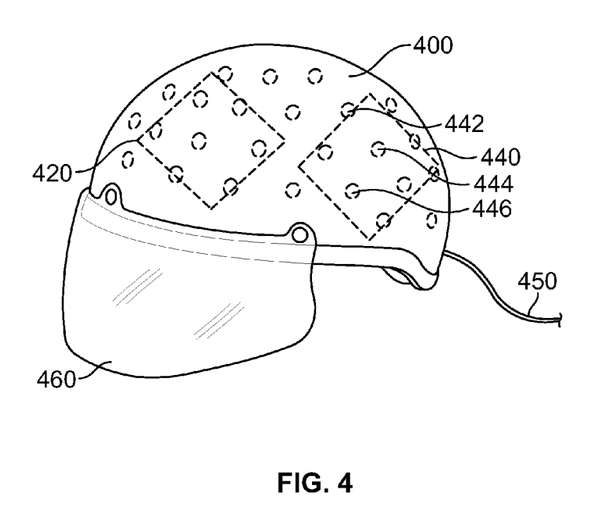
FIG. 4 illustrates one embodiment of a helmet with electrodes used in the taking of measurements.

As part of the data collection for client 306 processing, FIG. 4 shows a perspective view of a helmet with electrodes used in embodiments of the disclosed technology. The helmet 400 comprises multiple electrodes, such as electrodes 442, 444, and 446. As can be seen in the figure, a plurality of electrodes are spaced apart around the interior of a helmet or other piece of headgear and are adapted for both reading electrical activity from the brain of the wearer and delivering new impulses. That is, by way of a single electrode, plurality thereof, cluster of electrodes, or plurality of clusters, a joint brain electro-analysis and transcranial current stimulation system (tCS) comprises a plurality of spaced-apart removable and replaceable electrodes arranged in an item of headgear. An electroencephalography device (such as an EEG) is wired to each of the electrodes, as is a transcranial direct current stimulation device (at the same time or by way of a switch or plugging/unplugging a cable between the devices).

In one embodiment, cable 450 allows for electrical connectivity between the electrodes and either or both of a tCS and EEG device. In one embodiment, the cable may be eliminated using wireless connectivity and communication techniques. Further, a visor 460 is integrated with the helmet in embodiments of the disclosed technology for optical stimulation (e.g. a video monitor). The visor may be an embedded display, as illustrated in FIG. 4 or in another embodiment may include an auxiliary or augmented display, such as pair of glasses or an immersive screen technology, as described in further detail below.

Upon measuring an electroencephalography anomaly in a brain region with the electroencephalography device, transcranial direct current stimulation is engaged to at least one anode and at least one cathode electrode to the brain region where said anomaly was measured. Additional devices such as a force plate, visual stimuli utilizing interactive games and tests, and the like, may also be utilized.

As used herein, the tCS may be transcranial direct current stimulation (tDCS) or transcranial alternating current stimulation (tACS). The data collection techniques and operations, as described in U.S. patent application Ser. No. 13/742,066 and U.S. Pat. No. 8,380,316 and U.S. Pat. No. 8,239,030 are herein incorporated by reference.

The data is collected and thus provided to one or more remote data processing systems. These remote data processing systems may be connected via a networked connection, including in one embodiment an Internet-based connection. In additional embodiments, the networking may be via a private or secure network. Wherein, it is noted that Internet-based connections include the processing of security features with the data, to insure the privacy of the data during transmission.

For example, one embodiment may include a data collection computing device, such as a personal computer or other type of processing device, operative to receive the electrophysiology data. The processing device therein provides for the encryption or inclusion of security features on the data and the transmission to one or more designated locations. For example, one embodiment may include the compression of the data into a ".zip" file.

The server further provides for the storage of the data and retention of data information. In this embodiment, the server creates a postscript formatted file, such as a PDF file and the database is then updated to include storage of this information. In one embodiment the database further includes enhancements to maximize storage, including determining if the data to be stored is duplicative. If the data is duplicative, a single data link can be provided, but if the data is not duplicative, then separate access to the data is provided.

The data acquired from the device may be processed locally or across network. In a typical embodiment, the user or client is a doctor or other medical specialist having the ability to review, understand and advise a patient based on the data generated in the reports. As noted above, the data generated in the reports relate to the electrophysiology data acquired from patients.

The complete system consists of a wireless amplifier equipped to record artifact free electrical signals from the brain and heart and also position in space using a nine or greater accelerometer. This same device is configured to deliver electric current back to the sensors that are in contact with the scalp in order to facilitated non-invasive brain stimulation. Sensors make contact with this skin using either dry sensors or electro dermal gel or saline impregnated sensor for consistent sensor to skin connectivity measured by impedance.

The software provides for automated data collection using script software and self-guided instructions. The software sends the resulting data for algorithm processing either on the CPU or on a dedicated secure server through an internet connection. This data is processed on the CPU and processed either on the installed database and processing software or transmitted to the cloud-based server where processing takes place.

The data analysis is returned in a report format showing physiology graphics and interpretive results from which the user can make intervention or diagnostic decisions. Several comparison databases can be selected from within the software to provide a comparison measure for the data analysis. Pre-set EEG training protocols (e.g., theta:beta ratio training for attention; alpha:theta ratio training for relaxation) are configured for automated home or clinic based training.

Individual baseline data can also be utilized so that the individual's data can be compared to an earlier data sample. An example of this is a professional athlete having his or her pre-season baseline that is used for comparison following a concussion. This is particularly useful for single-subject design research of change over time and intervention results. Group databases such as peak performance or pathology comparison databases (i.e., Alzheimer's disease sample database) are also available for selection and data comparison. Intervention options include real-time noise and artifact removal algorithms that permit EEG and ECG training devoid of movement and other disruptive artifact or signal noise. Individual differences from the selected comparison database permits specific or individually derived interventions as non-invasive brain stimulation (e.g., tDCS/tACS) and brain computer interface (sLORETA/eLORETA brain computer interface, wavelet time-frequency neurofeedback, event-related potential neurofeedback; Brodman Area selection, neurofeedback, neuro-network brain computer interface) and peripheral biofeedback such as heart rate variability biofeedback).

The brain computer interface or neurofeedback can include any number of operations or techniques, including for example low resolution brain electromagnetic topography source localization feedback and surface electroencephalography amplitude or phase or coherence feedback.

The user receives report and intervention information from cloud-based server interface or from optional embedded software on the CPU for usage where internet connectivity is not possible.

The results of the data analysis include a protocol that directs the non-invasive brain stimulation sensor placements and current parameters. These stimulation protocols can be manually or automatically selected to provide the user with both brain compute interface training and brain stimulation or brain modulation interventions.

The rapid assessment and re-assessment of the brain and other measures included in the physiology measurement battery allows for rapid determination of brain computer interface training location and frequency protocols and also brain stimulation or modulation using electric current. The re-assessment quantifies the difference from the baseline measure in order to generate a report showing the change made by either or both brain computer interface and electric current brain modulation.

The re-assessment then provides an updated intervention protocol. Protocols will vary based on the assessment results such that the different locations on the scalp may be stimulated with different polarity at the sensor and with more or less milliamps than one another. Users can manually define scalp location, polarity at the sensor, and milliamp levels and duration at each location. Users can also select from pre-defined protocols to increase or decrease regional neuronal activity.

The same data analysis report provides illustration and instruction on the current flow through the brain tissue in order to further quantify the cortical excitability relevant to the users clinical or performance intent. Current flow reporting aid the user with further and more specific brain modulation targeting protocols using Talairach locations and Brodmann Areas. The availability of the data analysis and reports on the web portal allows for telemedicine access and review.

The sensors permit real time stimulation with electrical current and simultaneous recording of EEG using signal filters that remove the electrical stimulation and permit only the EEG and event related potentials to be recorded and processed. This feature permits the user to combine targeted brain stimulation with brain computer interface training using real time artifact correction. Simultaneous neurofeedback with stimulation allows for data analysis showing the focal changes or modulation in the brain from the individual or combined intervention modalities.

Figure 5:
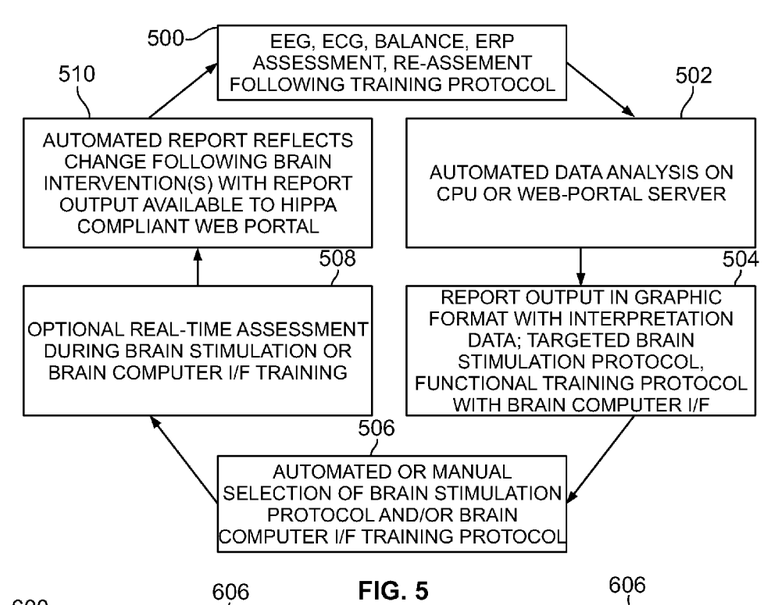
FIG. 5 illustrates one embodiment of a data flow cycle.

FIG. 5 illustrates a circular data flow diagram representing the circular operations described herein. Step 500 includes the assessment and re-assessment protocols, such as EEG, ECG, Balance, ERP, etc. Step 502 is the automated data analysis on a CPU or networked server. Step 504 is the report output, which may include output in graphical format with interpretation data. The report 504 may further include targeted brain stimulation protocol, functional training protocol with brain computer interface.

Continuing in the cycle of FIG. 5, step 506 is the automated or manual selection of brain stimulation protocol and/or brain computer interface training protocol. Step 508 is an optional real-time assessment during brain stimulation or brain computer interface training. Step 510 provides automated reporting that reflects changes following brain intervention(s) with report output, which can be available to a user including HIPAA-compliant web or network portals.

Figure 6:
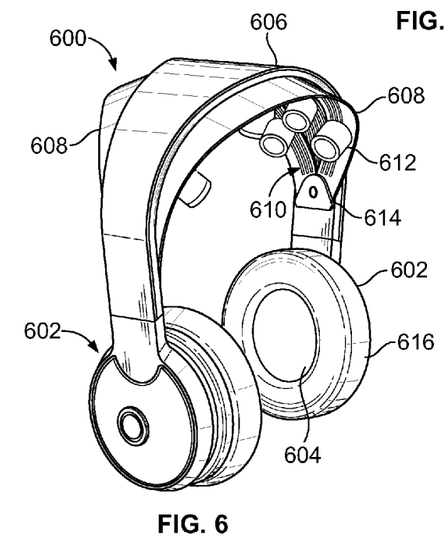
FIG. 6 illustrates a perspective view of one embodiment of a head gear device with electrodes for taking measurements.

FIG. 6 illustrates another embodiment of a device for collecting data and providing user feedback. This device 600 includes earpieces 602 with speakers 604. The device 600 further includes a top cross-bar 606 and side-bars 608, the bars, 606 and 608, having a track 610 thereacross with sensors 612 disposed therein. The device 600 additionally includes a hinge 614 for the side-bars 608. Further embodiments include an articulating arm 618 having a lens 620 thereon.

The headgear 600 may be composed of one or more suitable materials, including plastic, metal or carbon fiber by way of example. The earpieces 602 are representative embodiments of engagement portions providing for engaging the user's head and securing placement of the sensors 612. In the illustrated embodiment of FIG. 6, the speakers 604 are disposed within the engagement portions of the earpieces 602, providing for the audio output of sound consistent with known speaker technology. In this embodiment, the earpiece 602 and speaker 604 include cushioning 616 that not only improves user comfort in wearing the device, but also improves sound isolation of the speaker to minimize or reduce any ambient noise.

The cross bar 606 and side bars 608 include the track 610 that allows for the insertion of the sensors 612. The sensors 612 may be any suitable sensors that connect into the track for electrical connection with the device 600. In one embodiment, the sensors 612 are dry sensors, where the dry sensors are attached using magnets for easy removal and replacement in-between users and for alternate sensor or electrode type attachments. The same system both provides EEG/ERP measures but also delivers brain stimulation using direct current and/or alternating current, as described above.

When worn by a user, the sensors 612 are in contact with the user's cranium, wherein the location of the sensors 612 can be adjusted by movement of the sensor 612 along the track 610 within the cross-bars 606 and 608.

The hinge 612, disposed on both sides of the cross-bar 606, allows for the articulation of the of the side bars 608 away from or towards the cross-bar 608. Therefore, when worn by the user, the sensor 612 location of the user's cranium can also be adjusted by the inward or outward articulation of the side bars 608.

In embodiments including the arm 618 and the lens 620, the headgear 600 allows for the visual display of content on the lens 620. The positions or location of the lens 620 relative the user can be adjusted by the adjustment of the arm 618. The arm 618 includes wiring (not readily visible) for providing an output signal to the lens 620. In one embodiment, the lens 620 may be a high-definition lens operative to provide a visual output viewable by the user, where as described herein, the user can be subjected to visual stimuli for feedback generation via the headgear. In this embodiment, the lens 620 operates similar to the visual display goggles 104 of FIG. 1 or the visor 460 of FIG. 4.

Figure 7:
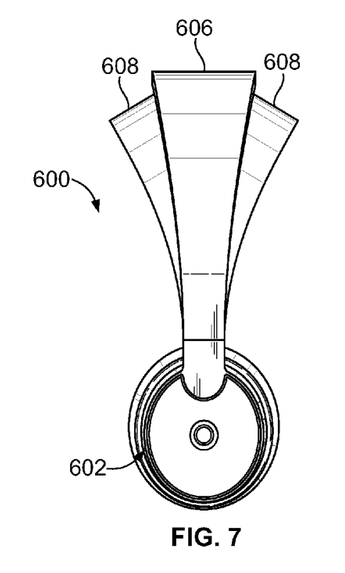
FIG. 7 illustrates a side view of the head gear device of FIG. 6.

FIG. 7 illustrates a side view of the headgear 600. The side view illustrates the inward or outward articulation of the cross-bars 608 from a centerline of the cross-bar 606. The headgear 600 can be worn similar to commercially available musical headphones. The side view additionally illustrates the ear covering portions 602. As described in further detail below, the earpiece 602 includes processing functionality allowing for electrophysiological measurements and interaction. Also visible in FIG. 7, the lens 620 extends outward via the arm 618.

Figure 8:
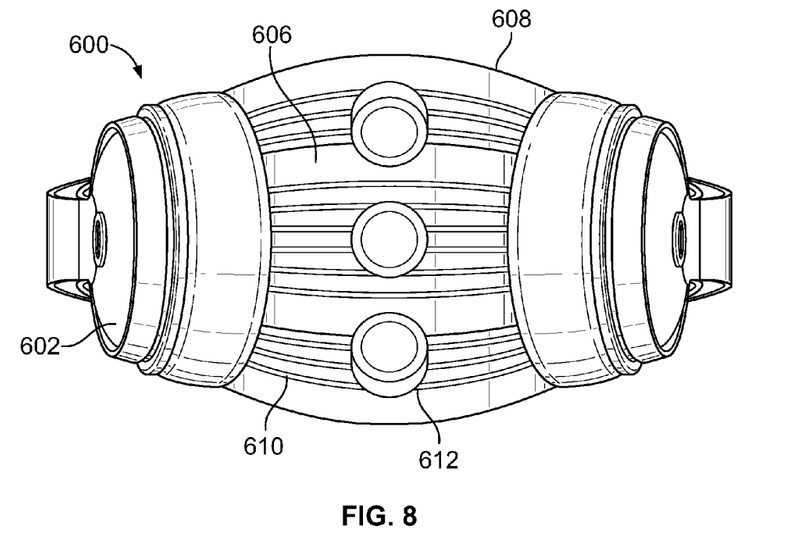
FIG. 8 illustrates an underside view of the head gear device of FIG. 6.

FIG. 8 illustrates a bottom or underside view of the headgear 600, including the earpieces 602, the cross-bar 606, the side bars 608, where the bars 606 and 608 include the tracks 610 and sensors 612. As illustrated, the tracks 610 extend across the bars 606, 608, allowing for adjusting the placement of the sensors 612. The sensors 612 can be located in the center (as illustrated), moved towards the left earpiece 602 or moved towards the right earpiece 602.

The location of the track further allows for the placement of multiple sensors 612 on the track 610, covering various regions of the user's cranium.

Figures 9, 10A, 10B:
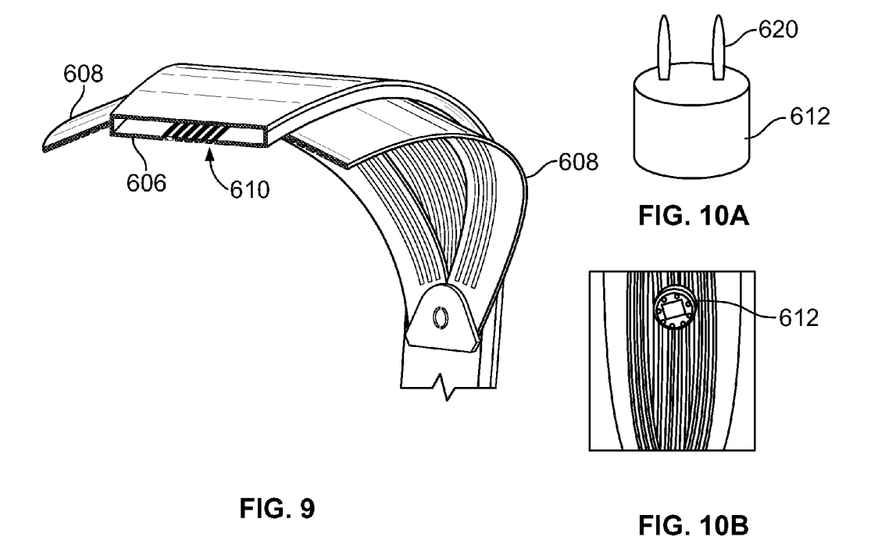
FIG. 9 illustrates a cut-away view of one embodiment of the track system of the head gear device of FIG. 6.
FIGS. 10a and 10b illustrate views of one embodiment of a sensor disposed within the headgear.

For further illustration of the track 610, FIG. 9 illustrates a cross-section of the bars 606, 608. In this embodiment, the tracks run along the interior side of the crossbars 606, 608, with a gap allowing for the insertion of the sensor therein.

FIG. 10*a* and FIG. 10*b* illustrate perspective views of one embodiment of the sensors 612. The top portion of the sensor 612 includes connection members 620 for passing through the openings of the tracks 610 and inserting into an electrical channel disposed within the bars 606, 608.

Figure 11:
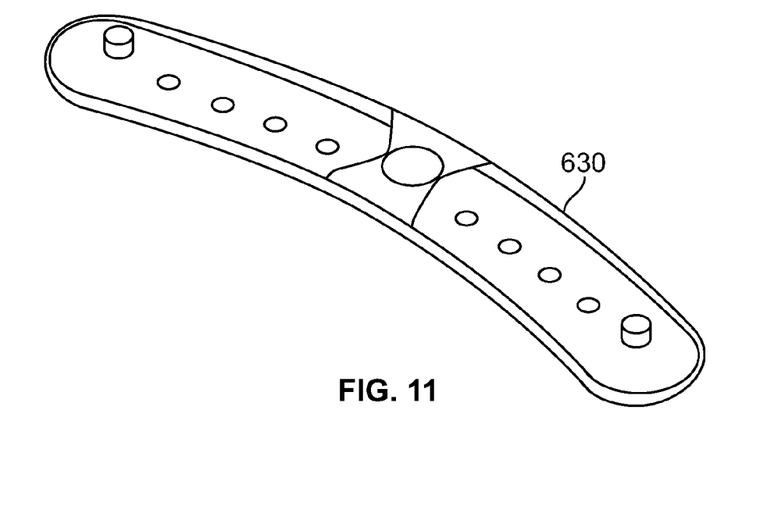
FIG. 11 illustrates a connector device disposed within a cross-bar of the headgear.

FIG. 11 illustrates one embodiment of an electrical channel 630 housing within the crossbars 606 and 608. The channel 630 includes at least two channels for passing current, such as alternative or direct current) to the sensors, as well as for transmitting feedback readings from the sensor to one or more control units.

In the assembly of the headgear 600, the sensor 612 snaps or engages the track 610 for being held in place, and the connectors 622 engage the electrical channel. The sensors 612 may be moved lengthwise across the arch of the bars 606, 608, for different cranium engagement points on the user wearing the headgear. In one embodiment, the dry sensors are attached using magnets for easy removal and replacement in-between users and for alternate sensor or electrode type attachments. The same system provides EMG, EEG and/or ERP measurements but also delivers brain stimulation using direct and alternating current.

FIG. 10*b* illustrates another perspective view of the sensor 612, illustrating the downward portion of the sensor 612 that engages the user's cranium. In this embodiment, the sensor 612 is a dry contact sensor that includes a plurality of contact pins or engagement pins that are operative to transmit current into the user's scalp and/or receiving measurements or readings from the user's scalp.

Figure 12:
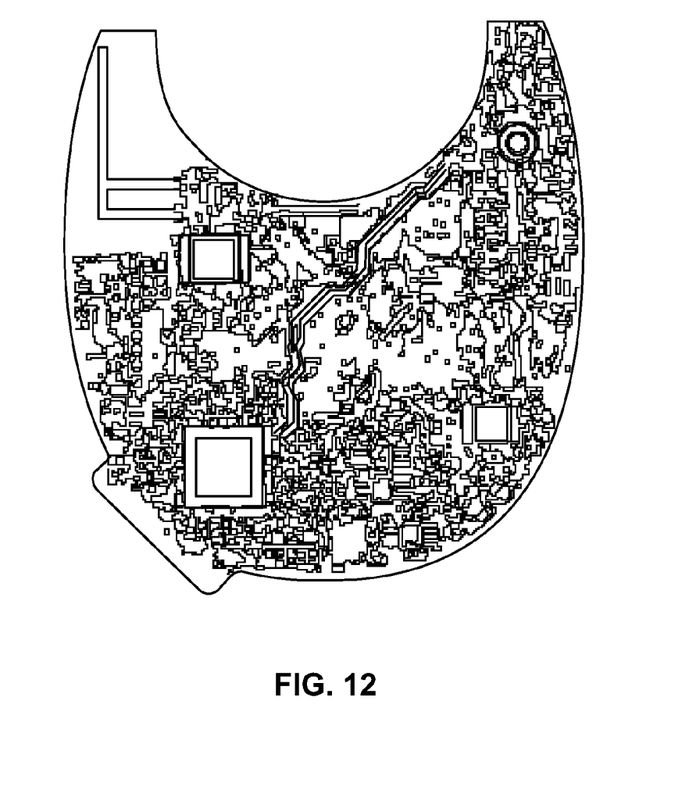
FIG. 12 illustrates one embodiment of a printed circuit board for functionality of the headgear device.

FIG. 12 illustrates one embodiment of a printed circuit board disposed within the earpiece 602 on the headgear 600. The printed circuit board includes processing operations for providing functionality as described herein. The circuit board includes, in one embodiment, wireless functionality allowing for the headgear 600 to not require a wired connection to a secondary computing device. In one embodiment, the printed circuit board provides functionality for engaging the sensors in determining optimized placement, as well as execution of electrophysiology interaction.

In further embodiments, the headgear includes additional functionality, which can be further beneficial for electrophysiological interaction. For example, the headgear may include a movement displacement sensor to detect head movement, as well as multi-dimensional plane orientation. For example, inclusion of displacement technology can help determine if the user is looking up, looking down, tilting his or her head, etc.

The combined hardware sensor array, firmware, and software within the headset device incorporates high quality microphone for voice commands and phone calls and includes high fidelity speakers for listening to auditory prompts and to listen to music. In one embodiment, materials are hypoallergenic. Headset is equipped with on-board circuitry for full signal processing and wireless transfer of data and real time clock and synchronization of stimulus presentation and measured physiology and balance or movement. In one embodiment, the headset is charged using contact charging points, where further embodiments may utilize any other suitable charging or re-charging technique. For example, in one embodiment, the headset includes a power engagement button for powering on and turning off the headset. In one embodiment, the power engagement button may be centrally located within an outside cover of the engagement portion.

Headset design permits multiple magnetic attached scalp sensor and proximity sensors that allow recording of EEG and ECG/BVP physiology data.

The headset has the advantage of being as fully functional as the higher end headphones but also adding brain computer interface and heart computer interface recording and modulation components. The device uses non-contact dry sensors to measure heart rate variability and EEG. The system can measure, record, and process within the headset circuitry the electrophysiology and transmit data in pre or post-processed form for remote cloud-based analysis or on the imbedded computer processing unit. Using real-time artifact correction algorithms the device is able to provide feedback to the user of EEG and blood volume pulse signal. The system further provides for EMG feedback and ECG feedback.

Video games are made further interactive with the condition of the human electrophysiology utilizing specific neuro-networks of the brain and particular regions of the brain responsible for different brain functions such as attention, language processing, memory processing, executive functions, affect, emotional processing. The lens 620 allows for the user to be placed in an immersive environment and engage in various degrees of interactivity.

One such example of interactivity is engaging video games where the user play can be directly influenced by the measured feedback from the headgear 100 or 600. For example, the game may integrate EEG features relative to the avatar or video game character, where those features are measured from the user.

Another example of interactivity is neuromarketing, whereby the headgear 600 allows for collection of neurological data relating to marketing. For example, data collection can include tracking users as they view commercials, collecting electrophysiology measurements. Another example may be having the user wear the device and actively enter a retail establishment or other arena in which the user is subjected to marketing, again measuring electrophysiology data.

Therefore, the headgear assembly improves upon prior headgear for not only data collection techniques, but also wearability. The inclusion of adjustability of the placement of the sensors provides a wider degree of usability and testability by displacing the sensors at various locations by adjusting the position of the sensors within the track and adjusting the position of the track over the user's cranium by articulating the bars 608.

While the disclosed technology herein references the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described herein are also contemplated and within the scope of the disclosed technology.

What is claimed is:

1. An apparatus for electrophysiology measurement, the apparatus comprising:
   a cross-bar having a first track disposed therein;
   a plurality of engagement portions disposed on opposing sides of the cross-bar;
   a first side-bar disposed between the engagement portions, the first side-bar having a first side track disposed therein; and
   a plurality of sensors attached to at least one of: the cross-bar and the first side-bar for contacting engagement with a head of a user for receiving electrophysiology measurements therefrom.

2. The apparatus of claim 1 further comprising:
   at least one hinge mechanism engaging the first side-bar to the cross-bar, whereby the at least one hinge mechanism allows for the articulation of the first side-bar relative to the cross-bar.

3. The apparatus of claim 2, wherein the plurality of sensors disposed in the first side-bar are disposed at a position within the first side-bar and the first side-bar is disposed at an articulated location from the cross-bar for directed contacting engagement with the head of the patient.

4. The apparatus of claim 1 further comprising:
   a second side-bar disposed between the engagement portions, the second side-bar have a second side track disposed therein.

5. The apparatus of claim 4 further comprising:
   at least one hinge mechanism engaging the first side-bar and the second side-bar to the cross-bar, whereby the at least one hinge mechanism allows for the articulation of the first side-bar and the second side-bar relative to the cross-bar.

6. The apparatus of claim 5, wherein:
   the plurality of sensors disposed in the first side-bar are disposed at a first position within the first side-bar and the first side-bar is disposed at a first articulated location from the cross-bar for directed contacting engagement with the head of the patient; and
   the plurality of sensors disposed in the second side-bar are disposed at a second position within the second side-bar and the second side-bar is disposed at a second articulated location from the cross-bar for directed contacting engagement with the head of the patient.

7. The apparatus of claim 1, wherein the engagement portion engages the ears of the patient, the apparatus further comprising:
   a plurality of speakers within engagement portions.

8. The apparatus of claim 7 further comprising:
   at least one processing device disposed within the engagement portions, the processing device in operative communication with an external processing system for electrophysiology measurements.

9. The apparatus of claim 8, wherein the operative communication is performed by at least one of: wireless communication and wired communication.

10. The apparatus of claim 7 further comprising:
an audio receiving device operative to receive audio input from the patient.

11. The apparatus of claim 1 further comprising:
a lens operative to display a visual display thereon, wherein the lens is disposed outward from the cross-bar by an arm.

12. The apparatus of claim 1 further comprising:
a magnetic portion disposed within the first track, the plurality of sensors includes a magnetic attachment portion such that the sensor engages the first track via a magnetic connection.

13. The apparatus of claim 1, wherein the sensors are dry sensors operative to perform transcranial current stimulation.

14. The apparatus of claim 12, wherein the transcranial stimulation includes at least one of: transcranial alternating current stimulation and transcranial direct current stimulation.

15. An apparatus for electrophysiology measurement, the apparatus comprising:
a cross-bar having a first track disposed therein;
a plurality of speakers disposed within engagement portions, the engagement portions disposed on opposing sides of the cross-bar;
a first side-bar disposed between the engagement portions, the first side-bar having a first side track disposed therein;
a second side-bar disposed between the engagement portions, the second side bar having a second side track disposed therein, the second side-bar on an opposing side of the cross-bar;
at least one hinge mechanism engaging the first side-bar to the cross-bar and the second side-bar to the cross-bar, allowing for the articulation of the first side-bar and the second side-bar relative to the cross-bar; and
a plurality of sensors attached to the cross-bar, the first side-bar and the second side-bar for contacting engagement with a head of a patient for receiving electrophysiology measurements therefrom.

16. The apparatus of claim 15 further comprising:
the plurality of sensors disposed in the first side-bar are disposed at a first position within the first side-bar and the first side-bar is disposed at a first articulated location from the cross-bar for directed contacting engagement with the head of the patient; and
the plurality of sensors disposed in the second side-bar are disposed at a second position within the second side-bar and the second side-bar is disposed at a second articulated location from the cross-bar for directed contacting engagement with the head of the patient.

17. The apparatus of claim 15 further comprising:
at least one processing device disposed within the ear engagement portions, the processing device in operative communication with an external processing system for electrophysiology measurements.

18. The apparatus of claim 15 further comprising:
an audio receiving device operative to receive audio input from the patient.

19. The apparatus of claim 15, wherein the first track, the first side-bar track and the second side-bar track include a magnetic portion, the apparatus further comprising:
the plurality of sensors include a magnetic attachment portion such that the sensors engage the first track, the first side-bar track and the second side-bar track, via a magnetic connection.

20. The apparatus of claim 15, wherein the sensors are dry sensors operative to perform transcranial current stimulation, wherein the transcranial stimulation includes at least one of: transcranial alternating current stimulation and transcranial direct current stimulation.

* * * * *